(12) United States Patent
Lu et al.

(10) Patent No.: US 8,399,751 B2
(45) Date of Patent: Mar. 19, 2013

(54) FUNCTIONAL ABIOTIC NANOSYSTEMS

(75) Inventors: Siyuan Lu, Los Angeles, CA (US);
Anupam Madhukar, Arcadia, CA (US);
Mark S. Humayun, Glendale, CA (US)

(73) Assignee: University of Southern California, Los Angeles, CA (US)

( * ) Notice: Subject to any disclaimer, the term of this patent is extended or adjusted under 35 U.S.C. 154(b) by 1163 days.

(21) Appl. No.: 12/138,289

(22) Filed: Jun. 12, 2008

(65) Prior Publication Data

US 2009/0088843 A1  Apr. 2, 2009

Related U.S. Application Data

(60) Provisional application No. 60/943,360, filed on Jun. 12, 2007.

(51) Int. Cl.
*A61K 9/14* (2006.01)

(52) U.S. Cl. ........ 977/925; 977/810; 977/811; 977/825; 977/904; 977/932; 977/949; 424/427; 424/489

(58) Field of Classification Search .................. 435/368, 435/36; 424/427, 489; 977/810, 811, 825, 977/904, 925, 932, 949
See application file for complete search history.

(56) References Cited

U.S. PATENT DOCUMENTS

| 6,194,213 | B1 * | 2/2001 | Barbera-Guillem | 435/7.21 |
|---|---|---|---|---|
| 8,290,714 | B2 * | 10/2012 | Ignatius et al. | 702/19 |
| 2002/0127224 | A1 * | 9/2002 | Chen | 424/130.1 |
| 2003/0022374 | A1 * | 1/2003 | Greenbaum et al. | 435/455 |
| 2006/0113557 | A1 | 6/2006 | Wojtczuk et al. | |
| 2007/0028928 | A1 | 2/2007 | Peyman | |

FOREIGN PATENT DOCUMENTS

| WO | WO 2006037226 A1 * | 4/2006 |
|---|---|---|
| WO | WO 2006096835 A2 * | 9/2006 |

OTHER PUBLICATIONS

Winter, Jo et al. Recognition molecule directed interfacing between semiconductor quantum dots and nerve cells. Advanced Materials. 2001. 13(22): 1673-1677.*
Kotlarchyk, M. "Electromagnetic radiation and interactions with matter." in: Encyclopedia of Imaging Science and Technology [online]. Published online: Jan. 15, 2002. [retrieved on Aug. 25, 2011]. Retrieved from Wiley Online Library using Internet <URL:http://onlinelibrary.wiley.com/doi/10.1002/0471443395.img017/full>.*
Lu, Siyuan. Some studies of nanocrystal quantum dots on chemically functionalized substrates (semiconductors) for novel biological sensing. PhD Dissertation, University of Southern California, 2006. 381 pages. Published on Dec. 1, 2006.*
DeMiguel et al., "Proofs of the Structure of Lipid Coated Nanoparticles (SMBV) used as Drug Carriers" Pharmaceutical Research, vol. 17, pp. 817-824, 2000.
International preliminary report on patentability for corresponding PCT application PCT/US08/66783 lists the reference above, May 20, 2010.
PCT International Search Report mailed Sep. 8, 2008 based on PCT/US08/66783.

* cited by examiner

*Primary Examiner* — Allison Ford
*Assistant Examiner* — Susan E Fernandez
(74) *Attorney, Agent, or Firm* — DLA Piper LLP (US)

(57) ABSTRACT

The invention relates to imparting photoreactivity to target cells, e.g., retinal cells, by introducing photoresponsive functional abiotic nanosystems (FANs), nanometer-scale semiconductor/metal or semiconductor/semiconductor heterojunctions that in this case include a photovoltaic effect. The invention further provides methods of making and using FANs, where the hetero-junctions bear surface functionalization that localizes them in cell membranes. Illumination of these hetero-junctions incorporated in cell membranes generates photovoltages that depolarize the membranes, such as those of nerve cells, in which FANs photogenerate action potentials. Incorporating FANs into the cells of a retina with damaged photoreceptor cells reintroduces photoresponsiveness to the retina, so that light creates action potentials that the brain interprets as sight.

19 Claims, 15 Drawing Sheets

FUNCTIONAL ABIOTIC NANOSYSTEMS

CROSS-REFERENCE TO RELATED APPLICATIONS

This application claims the benefit of Provisional Application No. 60/943,360, filed Jun. 12, 2007, entitled "FUNCTIONAL ABIOTIC NANOSYSTEMS". The benefit under 35 USC §119(e) of the U.S. provisional application is hereby claimed. The above priority application is hereby incorporated herein by reference.

STATEMENT OF FEDERALLY SPONSORED RESEARCH AND DEVELOPMENT

The U.S. Government has certain rights in this invention pursuant to grant No. EEC-0310723, awarded by the National Science Foundation, Engineering Research Centers Program and AFOSR 49620-01-0474 awarded by the Department of Defense.

FIELD OF THE INVENTION

The invention relates to methods to modulate the membrane potential of nerve cells upon light stimulation through use of chemically-synthesized functional abiotic nanosystems, and the application thereof to endow light sensitivity to retinal cells such as ganglion cells and bipolar cells and thereby restore lost visual response.

BACKGROUND OF THE INVENTION

Degenerative retinopathies such as age-related macular degeneration or retinitis pigmentosa are leading causes of blindness world-wide. Both pathologies involve the loss of function in photoreceptor cells in the retina. As such, partial or complete blindness often results even though the neural wiring connecting the eye to the brain is intact.

Accordingly, one approach to overcome blindness has been focusing on the development of photosensitive implants to bypass the damaged photoreceptors in blind patients. Exemplary microelectronics-based macroscopic implants operate similarly to cochlear implants for hearing loss by providing electrode-induced electrical stimulation of the ganglion cells that in turn provide signals to the optic nerve. The retinal ganglions so stimulated electrically convey signals to the brain, and thereby afford blind patients limited vision. While encouraging, such macroscopic implants are far from ideal. Physically, they are still very limiting in terms of their size, weight, and external power requirements. Functionally, they are suffer from the problem that the patient's field of vision moves with every head movement.

US 20030022374 describes an alternative approach in which the photoresponsiveness of the photoreceptors is restored. In this approach, an optical trigger such as a photosystem I reaction center is incorporation into a cell.

US 20070028928 describes a more general approach involving the localization of nano- and micro-particle solar cells within and among excitable biological cells to controllably regulate membrane polarization of such cells.

Presently, no treatment is available for restoring vision lost to retinitis pigmentosa or age-related macular degeneration. Thus, there still exists an unmet need for a way to treat such debilitating diseases.

SUMMARY OF THE INVENTION

The invention relates to imparting photoreactivity to target cells, e.g., retinal cells, by introducing photoresponsive functional abiotic nanosystems (FANs), nanometer-scale semiconductor/metal or semiconductor/semiconductor heterojunctions that in this case include a photovoltaic effect. The invention further provides methods of making and using FANs, where the hetero-junctions bear surface functionalization that localizes them in cell membranes. Illumination of these hetero-junctions incorporated in cell membranes generates photovoltages that depolarize the membranes, such as those of nerve cells, in which FANs photogenerate action potentials. Incorporating FANs into the cells of a retina with damaged photoreceptor cells reintroduces photoresponsiveness to the retina, so that light creates action potentials that the brain interprets as sight.

Other aspects and advantages of the invention will be apparent from the following description and the appended claims.

DETAILED DESCRIPTION

Unless otherwise specified, technical terms here take their usual meanings, specifically those specified in the McGraw- Hill Dictionary of Scientific and Technical Terms, 6th edition. The terms "plasma membrane" and "cell membrane" are used interchangeably throughout to refer to the lipid barrier between the interior and exterior of a eukaryotic cell.

Figure 1:
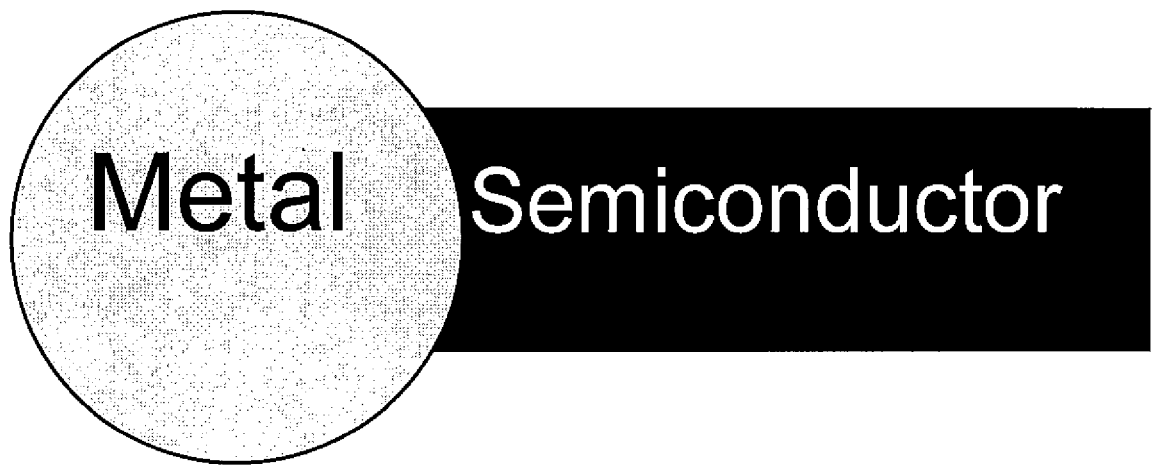
FIG. 1 shows a schematic diagram of an exemplary nanometer-sized semiconductor/metal junction.
Figure 2:
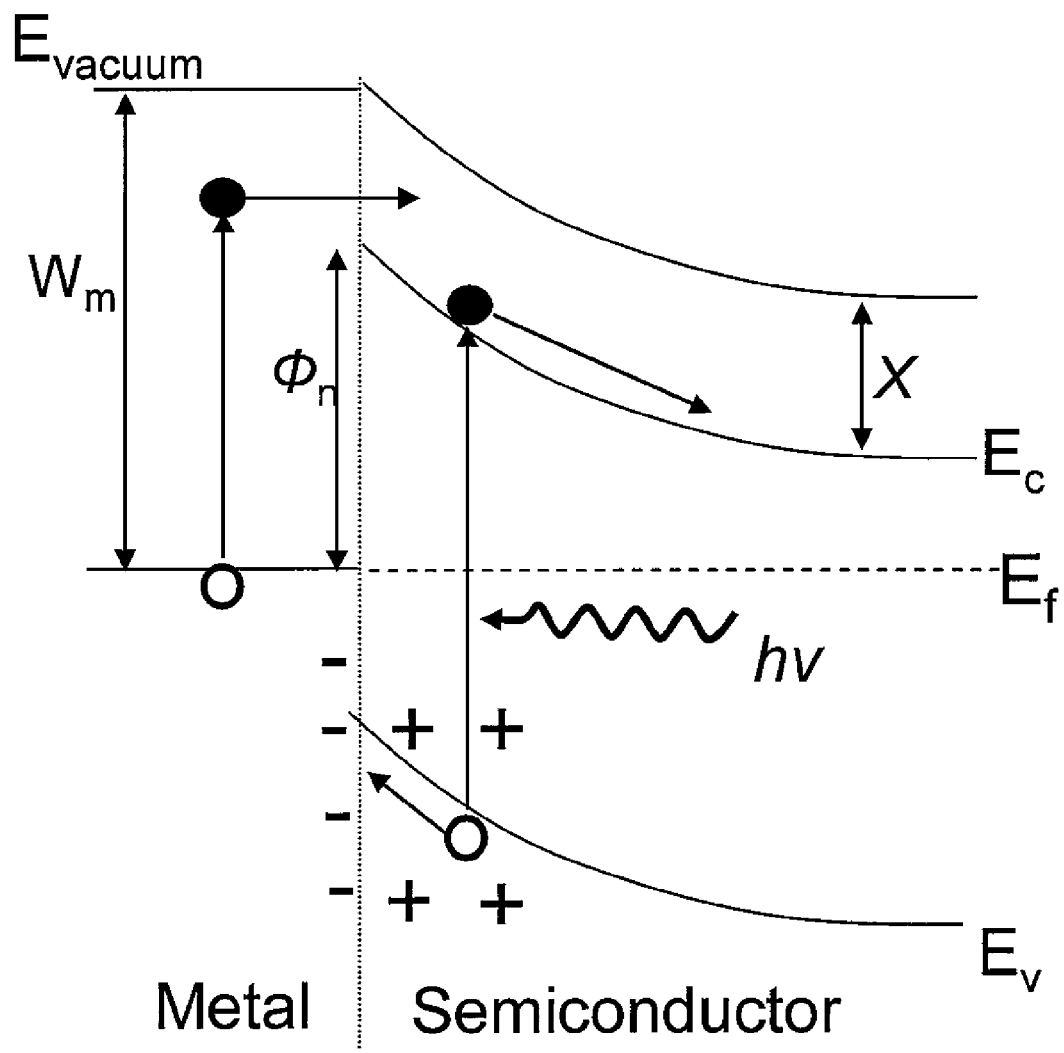
FIG. 2 shows a schematic representation of an exemplary band structure of a semiconductor/metal junction (Schottky junction) and its photovoltaic effect.

The present invention introduces photosensitivity into retinal ganglion cells via the attachment or insertion of FANs either across cell membrane or on the outer/inner surface of the cell membrane. FIG. 1 shows one embodiment of a photoresponsive FAN made of nanometer-sized semiconductor conjoined with a nanometer-sized metal, which together act as a photodiode. The difference in the chemical potentials of the two components (the semi-conductor and the metal) bends the energy bands of the semiconductor near the junction, creating a built-in electrical field. The corresponding schematic band structure of the resulting Schottky junction is shown in FIG. 2. Illumination creates electron-hole pairs that separate under the influence of the built-in field, thereby yielding a photovoltage across the structure (the photovoltaic, or PV, effect).

Figure 3:
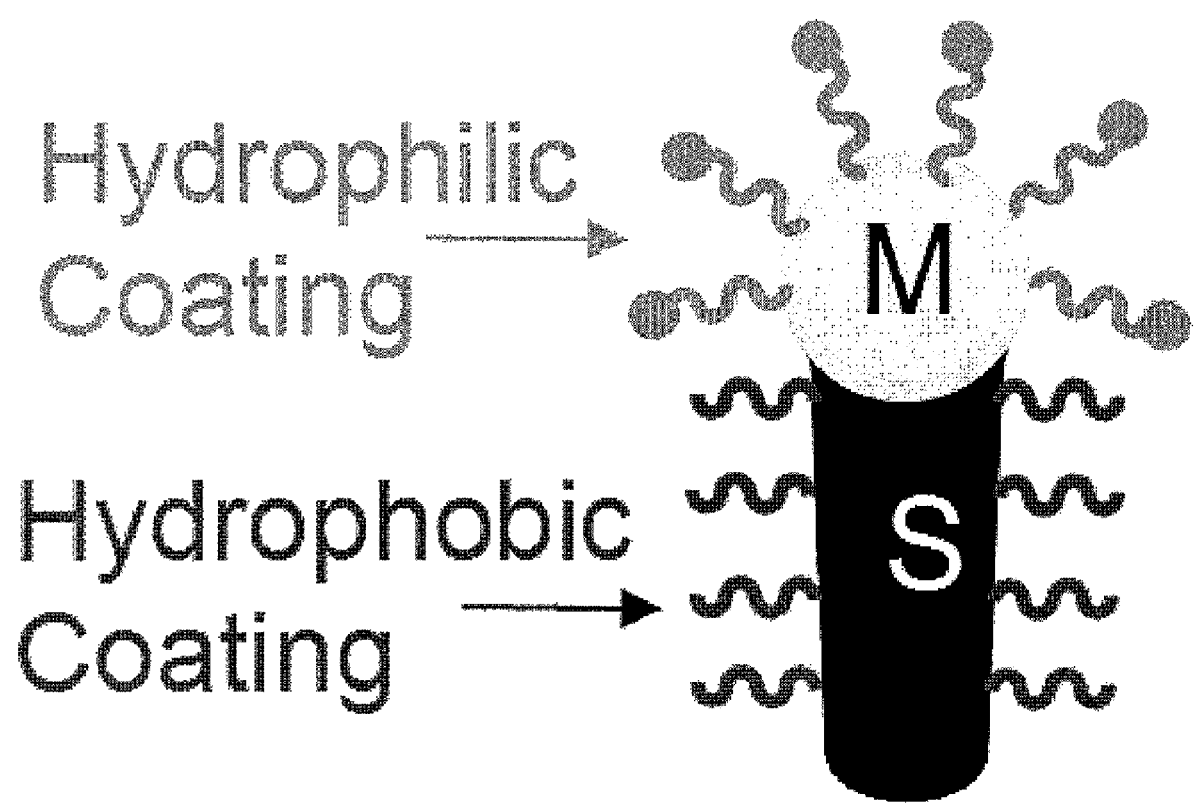
FIG. 3 shows a schematic representation of semiconductor/metal nanometer-sized hetero-junction-based FAN with amphiphilic functionalization.

FIG. 3 shows a schematic diagram of the amphiphilic functionalization of a semiconductor/metal hetero-junction, with the metal and semiconductor segments bearing hydrophilic and hydrophobic coatings, respectively.

Figure 4:
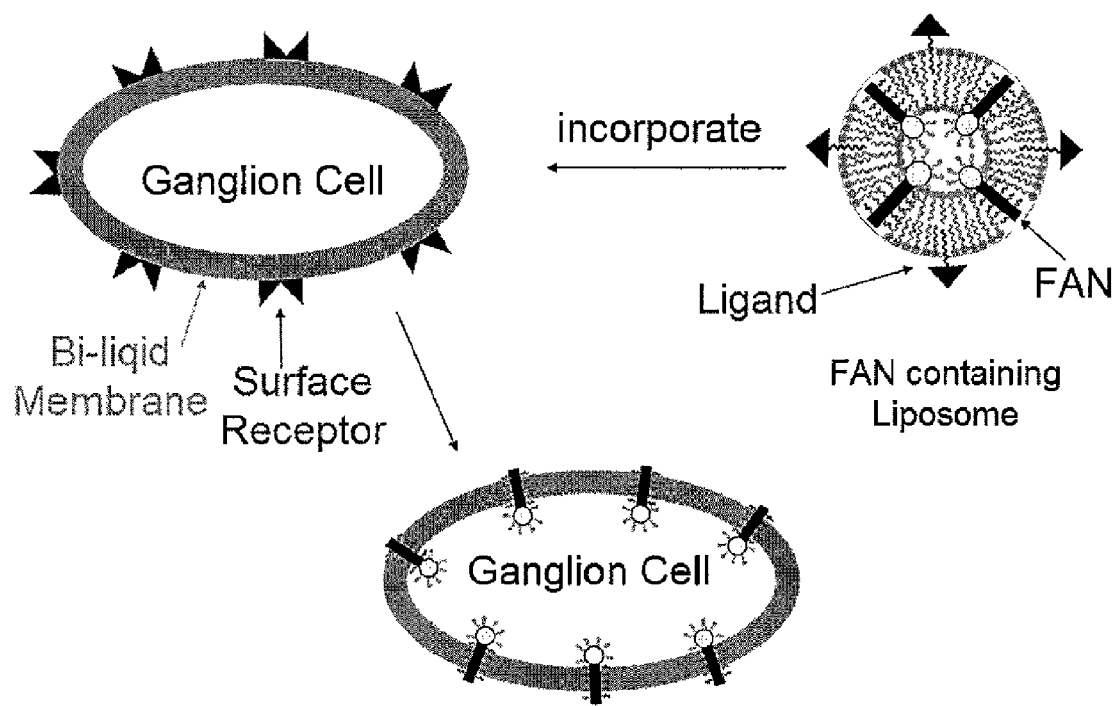
FIG. 4 shows a schematic representation of an exemplary method of inserting FANs into cell plasma membrane through use the of liposomes.

FIG. 4 schematically illustrates an exemplary approach in accordance with embodiments of the present invention for introducing a FAN to a retinal ganglion cell through the use of liposomes. After incorporation of amphiphilic FANs into a bilayer membrane of a liposome, assimilation of the liposome into a cell membrane delivers the FANs into that membrane, with the hydrophobic portion of each FAN immersed in the lipid portion of the membrane, and the hydrophilic extending into the aqueous phase.

Figure 5:
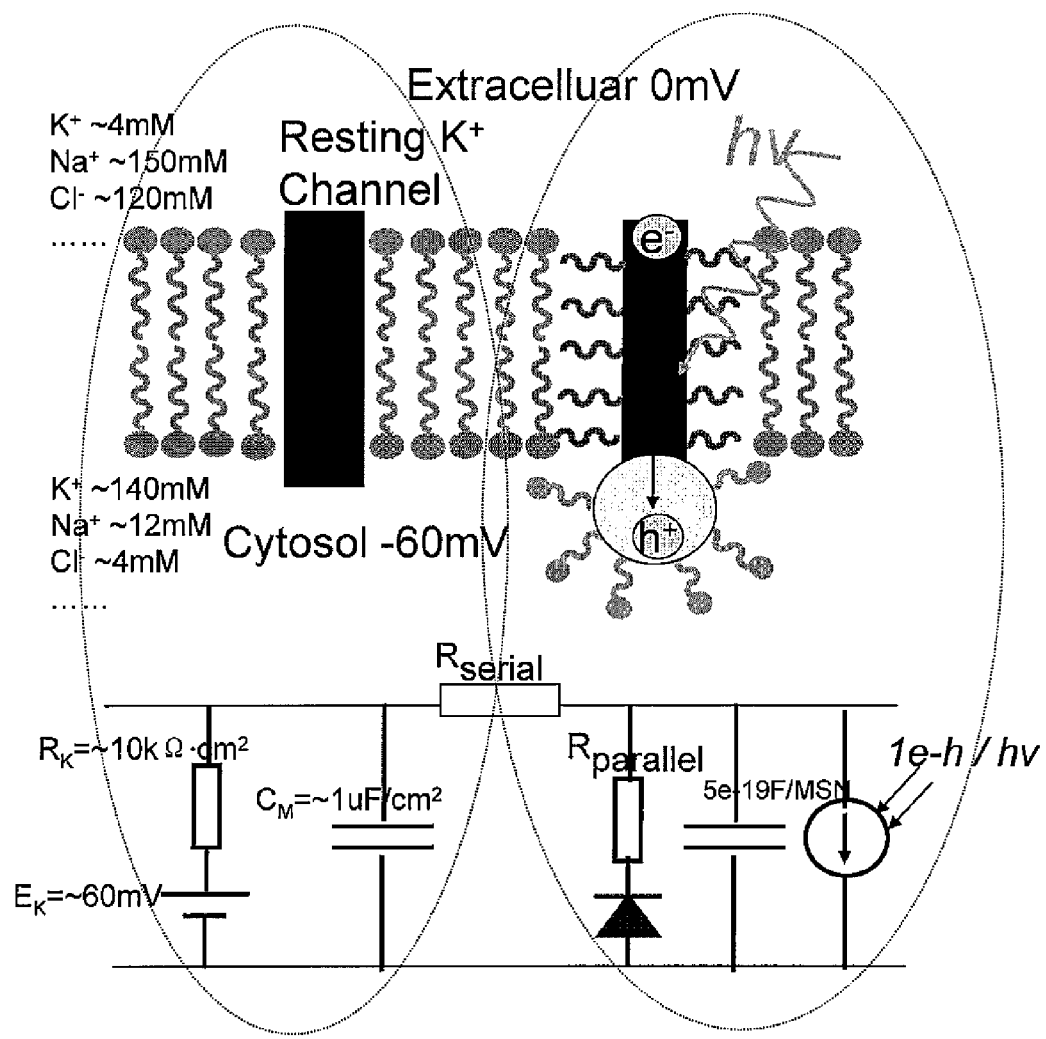
FIG. 5 shows a schematic diagram of a membrane with an embedded nanometer-sized hetero-junction FAN and of the equivalent circuit diagram.

FIG. 5 schematically shows how an FAN localized in a cell membrane, such as that of a ganglion cell, owing to its amphiphilic surface chemistry depolarizes the trans-membrane potential upon absorption of light. Excitation of the FAN with light generates a photovoltage that counteracts the transmembrane potential, triggering an action potential in the cell. The lower part of the figure shows the equivalent electronic circuit, with notional values of the electrical parameters of the circuit components.

Figure 6:
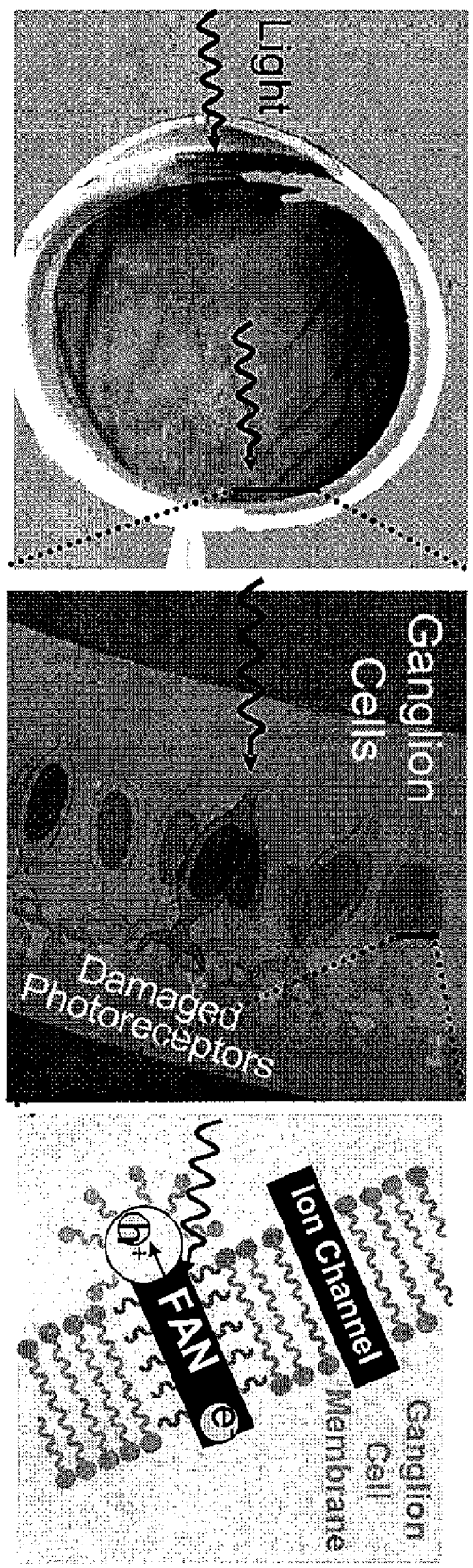
FIG. 6 is a schematic diagram showing FAN embedded into retinal ganglion cell membrane to endow photosensitivity.

FIG. 6 shows a schematic diagram of how a FAN embedded into a retinal ganglion cell membrane endows the cell with photosensitivity. Light traverses the anterior structures of the eye until impinging on the retina, where the light strikes retinal ganglion cells. Incorporation of FANs into retinal ganglion cell membranes allows light-induced signals to bypass damaged photoreceptors and generate a ganglion cell action potential triggered by the photovoltaic effect in the FAN.

Figure 7:
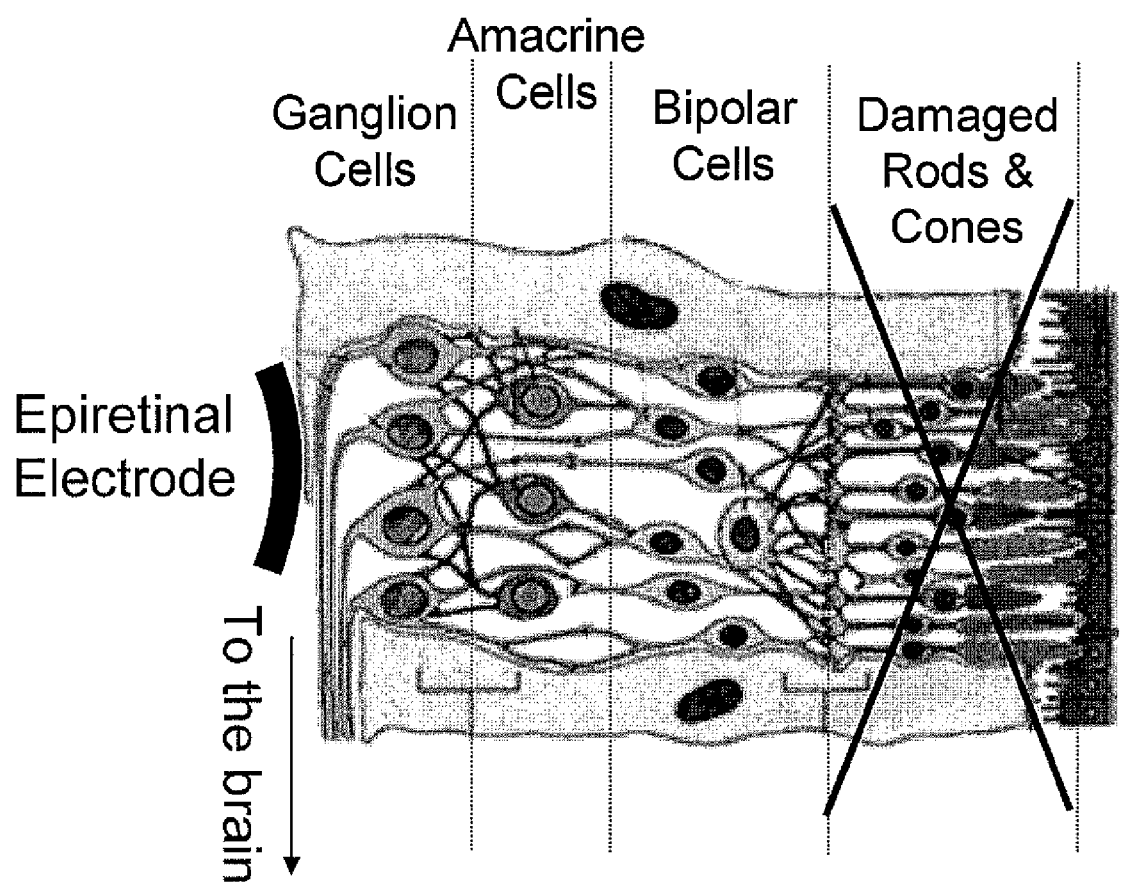
FIG. 7 is a schematic representation of the anatomy of the retina, showing its inverted nature. The ganglion cells are closer to the implanted electrodes.

FIG. 7 shows a detailed schematic view of the anatomy of the posterior region of the eye, including the ganglion cells connecting to the brain. Damaged retinal photoreceptors (rods and cones) are connected via bipolar and amacrine cells to the ganglion cells that transmit visual impulses to the brain. FAN-mediated intracellular stimulation of the ganglion cells bypasses damaged photoreceptors by triggering an action potential in the ganglion cells.

Figure 8:
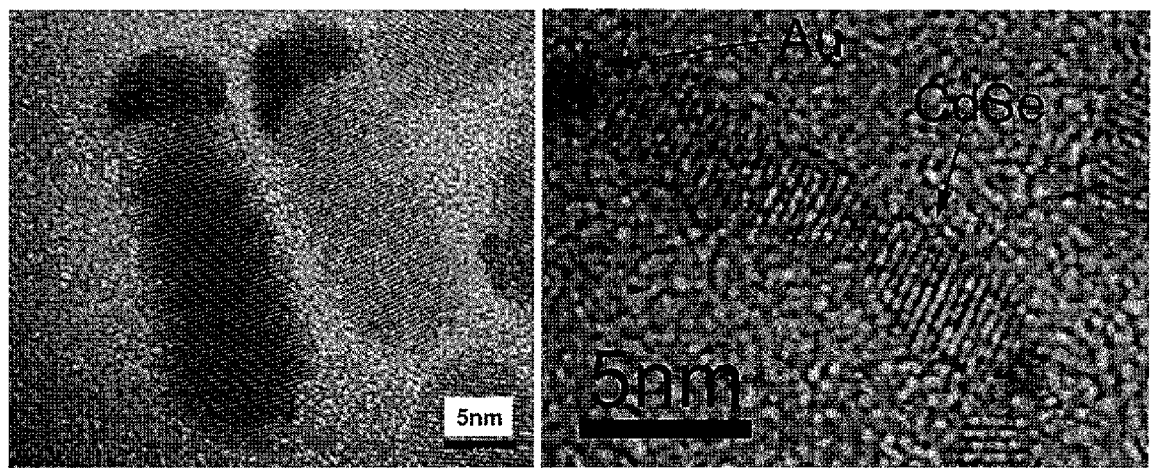
FIG. 8 shows high resolution transmission electron micrographs of two batches of CdSe/Au nanometer-sized semiconductor/metal hetero-junctions before micellar encapsulation.

FIG. 8 shows high resolution transmission electron micrographs of two batches of CdSe/Au nanometer-sized semiconductor/metal hetero-junctions of different sizes (left ~30 nm long; right ~15 nm long) before micellar encapsulation. The Au tip of the rod appears darker than the CdSe end owing to its higher electron density. Evenly spaced CdSe lattice planes show that Au growth does not compromise the integrity of the CdSe portion.

Figure 9:
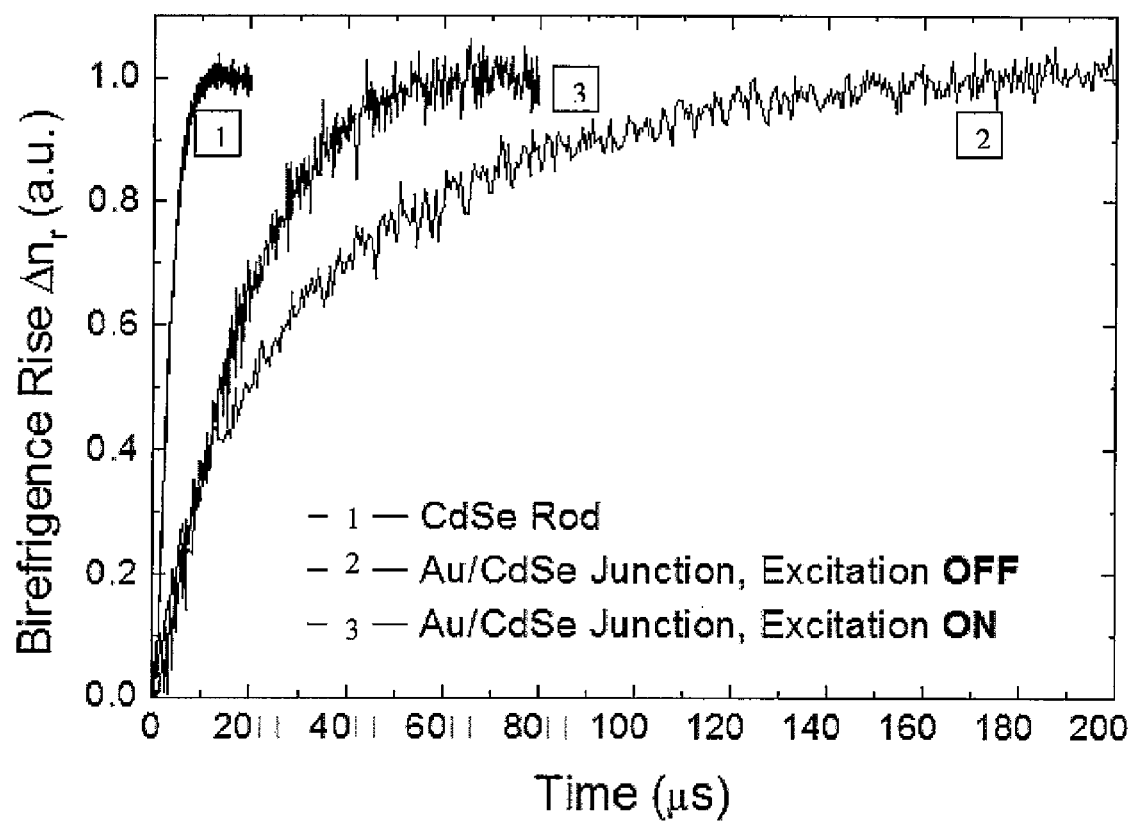
FIG. 9 depicts the rise of birefringence upon application of external electrical field of CdSe rods, Au/CdSe nanometer-sized hetero-junctions with and without light excitation.
Figure 10:
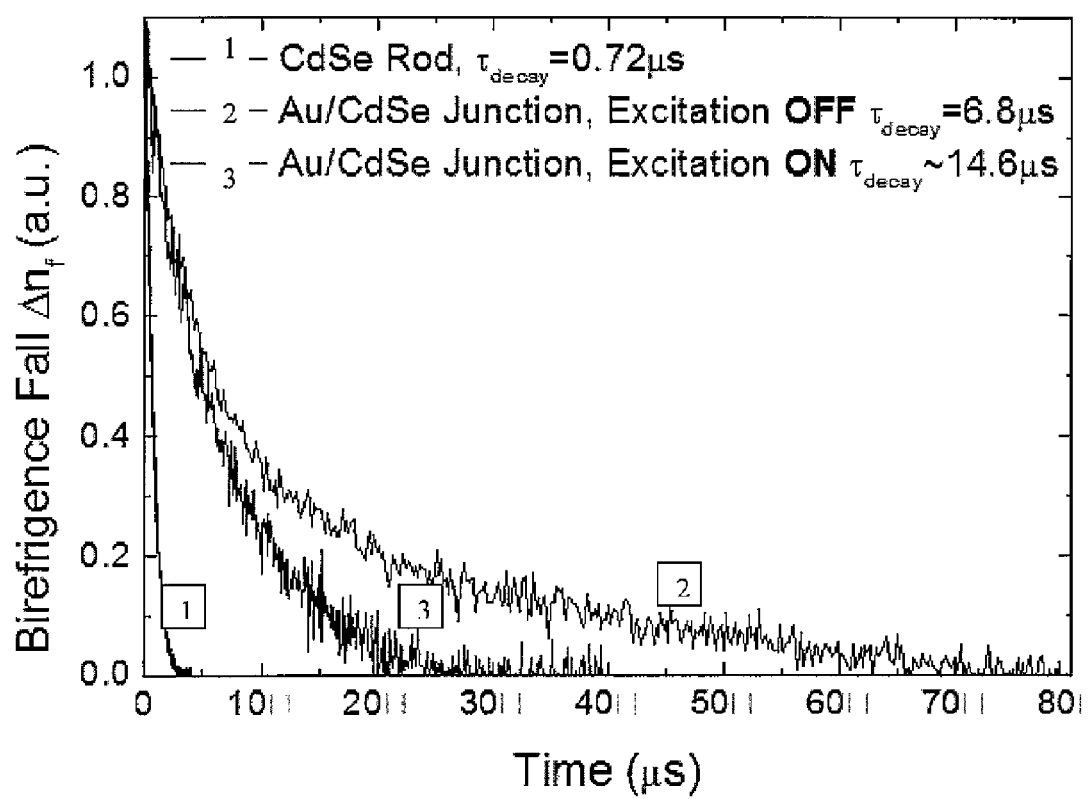
FIG. 10 depicts the fall of birefringence upon removal of external electrical field of CdSe rods, Au/CdSe nanometer-sized hetero-junctions with and without light excitation.

FIG. 9 and FIG. 10 show the birefringence upon application and removal, respectively of external electrical field of CdSe rods, and of Au/CdSe nanometer-sized hetero-junctions with and without light excitation.

Figure 11:
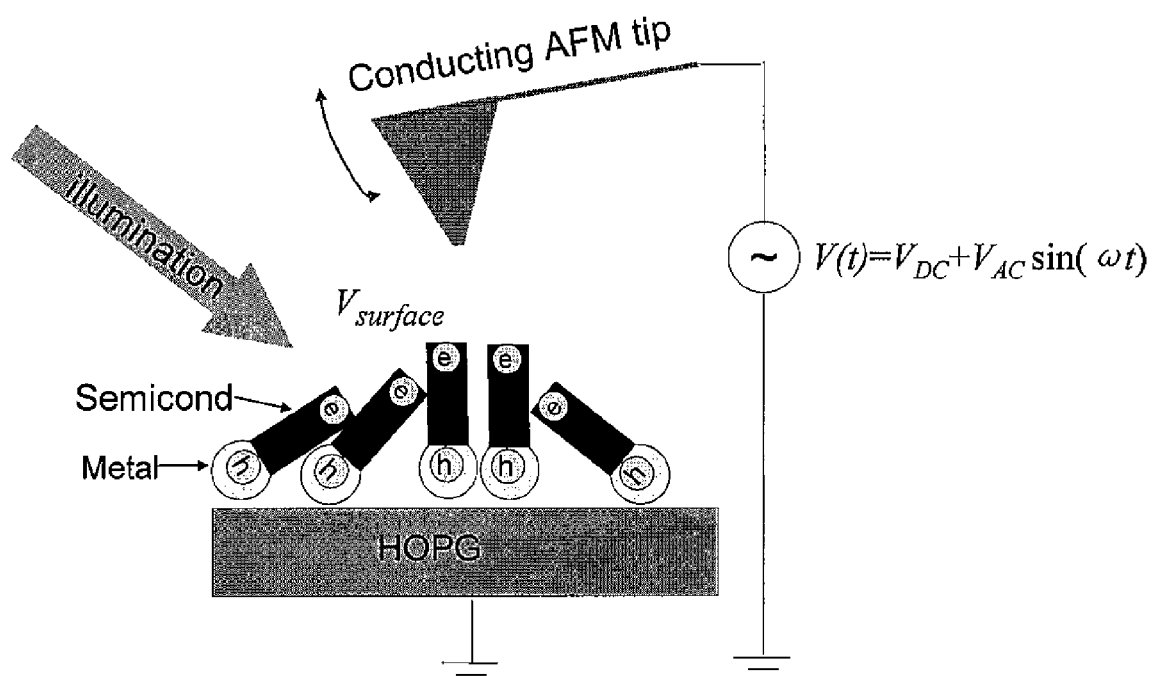
FIG. 11 is a schematic diagram showing an exemplary experimental setup for probing the PV effect of FANs using AFM based surface potential probing (SPP).

FIG. 11 is a schematic showing the experimental setup used to probe the photovoltaic effect of FANs using atomic force microscopy based surface potential probing (SPP).

Figure 12:
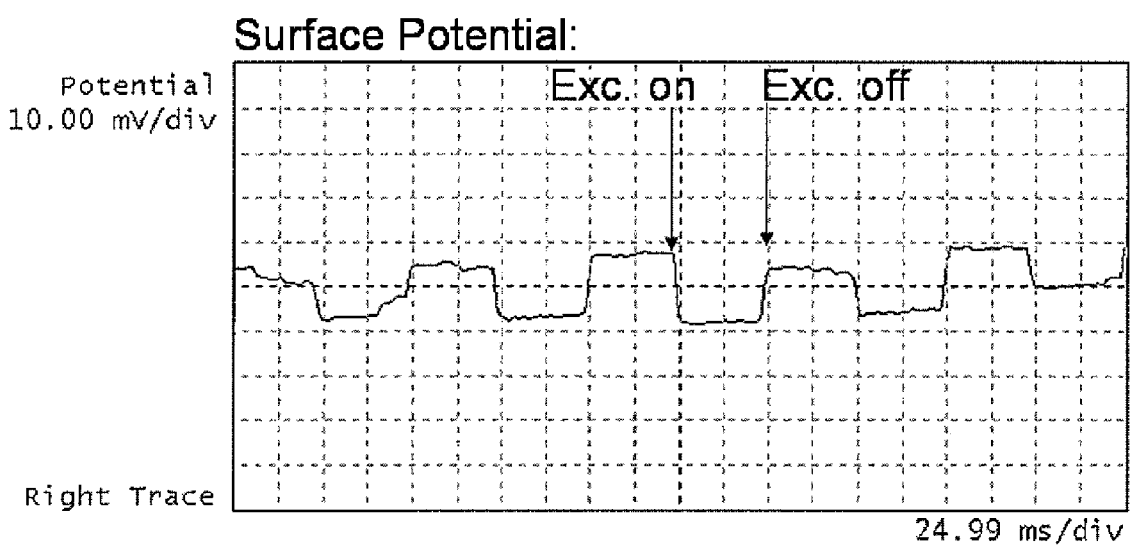
FIG. 12 shows measured surface potential change of FAN coated HOPG when light illumination is turned on and off.

FIG. 12 shows the measured surface potential change of FAN coated HOPG substrate under illumination of 532 nm laser chopped at 10 Hz. A surface potential difference of ~15 mV was observed when illumination is turned on and off. This difference may be attributed to the photovoltaic effect of the FANs.

Figure 13:
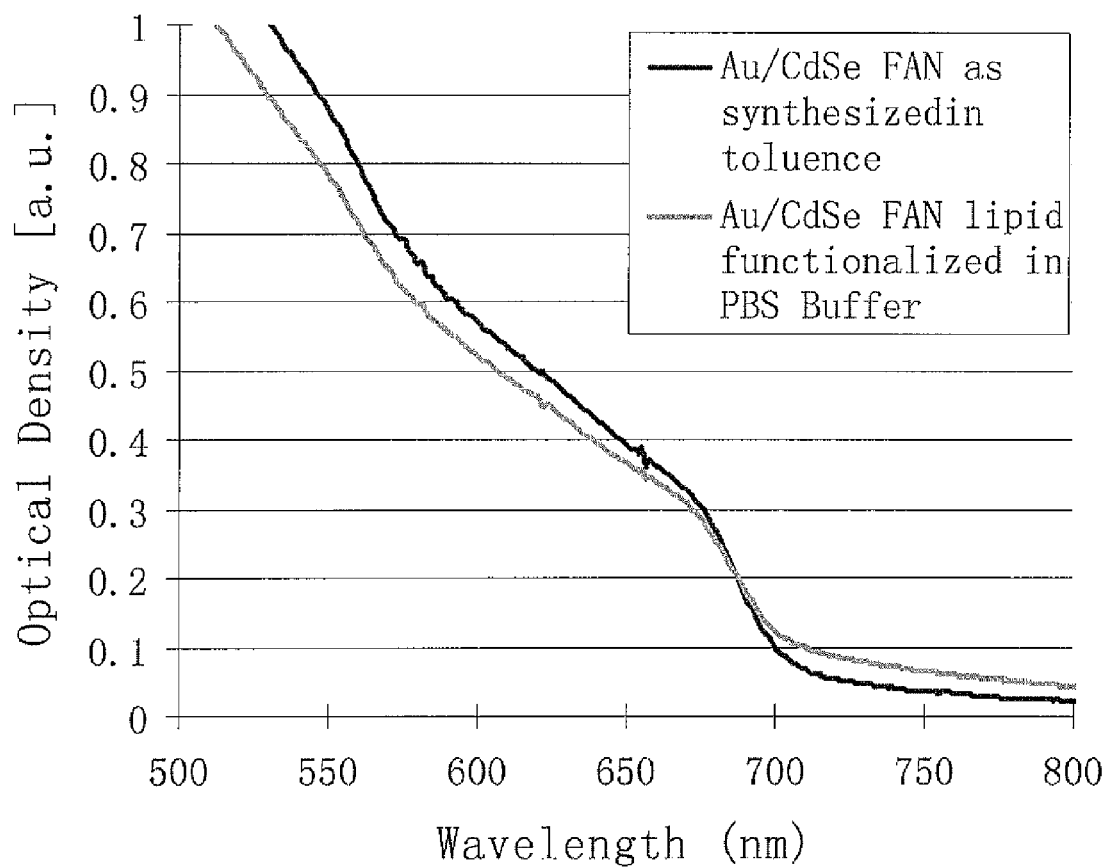
FIG. 13 shows an exemplary absorption spectra of Au/CdSe FANs before (in toluene) and after (dissolved in phosphate-buffered saline solution) micellar encapsulation.

FIG. 13 shows the optical absorption spectra of CdSe/Au FANs as synthesized (in toluene), and in phosphate-buffered saline after functionalization, showing that the optical properties of the FANs remain largely unchanged by the derivatization procedure.

Figure 14:
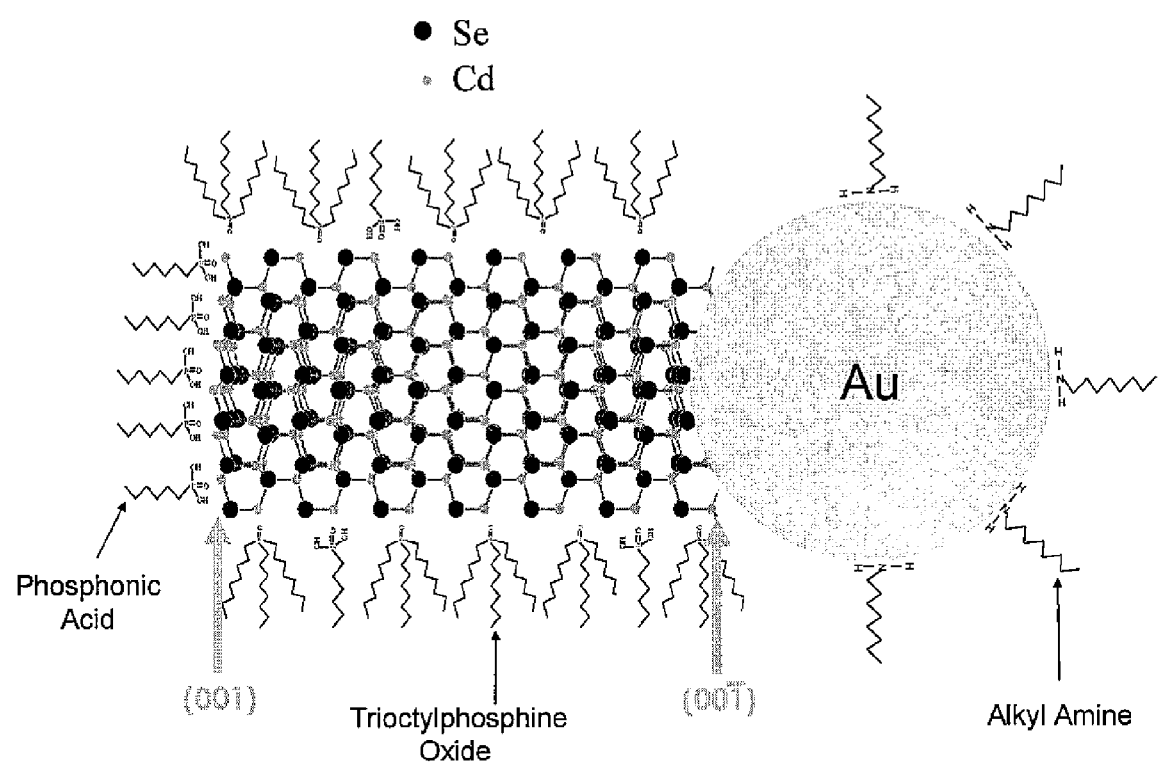
FIG. 14 is a schematic diagram showing the ligands covering different facets of an exemplary as-synthesized semiconductor/metal (CdSe/Au) hetero-junctions.

FIG. 14 schematically shows the CdSe/Au rods as synthesized, when they are covered by trioctylphosphine oxide and alkylphosphonic acid (both of which are hydrophobic).

Figure 15:
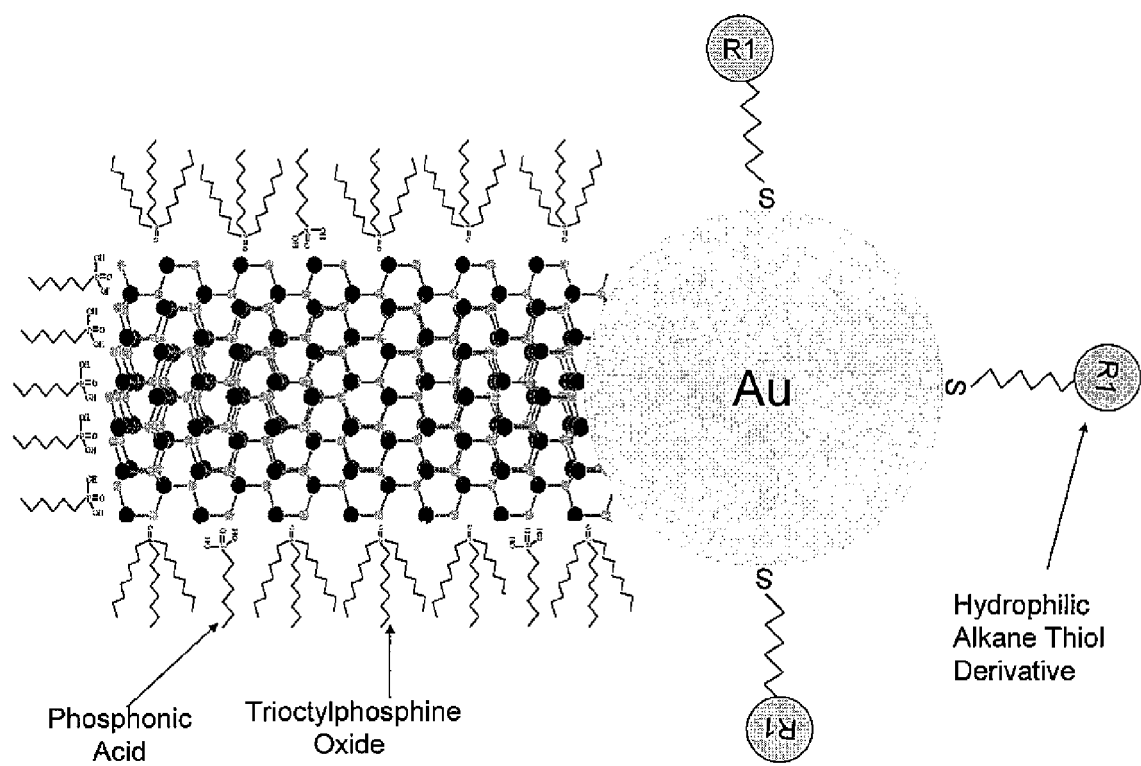
FIG. 15 is schematic diagram showing an exemplary approach to modify surfaces of the semiconductor/metal (CdSe/Au) hetero-junctions.

FIG. 15 schematically illustrates that, after surface functionalization with polyethylene glycol, the surface of the Au portion of the CdSe/Au FAN is hydrophilic, while the CdSe end, still covered by trioctylphosphine oxide and alkyl phosphonic acid, remains hydrophobic.

Illumination of photovoltaic FANs embedded into a nerve cell membrane changes the potential across the nerve cell membrane by ~10 mV and thereby triggers the firing of an action potential. US 20030022374 (hereby incorporated by reference in its entirety) discloses that illumination of spinach photosystem I particles (~50 nm in size), delivered to retinoblastoma cells through the use of proteoliposome vesicles, changes the $Ca^{2+}$ concentration gradient across the plasma membrane of the cells. US 20070028928 (also incorporated by reference in its entirety) describes methods of using nanoparticle solar cells to regulate the membrane polarization of excitable biological cells.

Incorporation of Photovoltaic FANs into Cell Membranes

Placement and stabilization of the photovoltaic FAN actuators in the membrane mimics the naturally-occurring amphiphilic trans-membrane proteins, which have hydrophobic membrane-spanning domain(s) that interact with fatty acyl groups of the membrane phospholipids and hydrophilic domains extending into the aqueous medium on each side of the membrane. Nanometer-sized semiconductor/metal hetero-junction FANs have different surface chemistry at the metal and semiconductor components. This allows the two to be functionalized separately with hydrophilic and hydrophobic compounds (FIG. 3), thus making them amphiphilic for trans-membrane anchoring.

Delivery of the nanometer-sized hetero-junction photovoltaic FAN to targeted cells and other locations is achieved through the use of liposomes (FIG. 4). Amphiphilically-functionalized FANs are incorporated into phosphilipid liposomes through the use of standard procedures. When the liposomes are fused with the cells, the nanometer-sized hetero-junction are inserted into the cell plasma membrane. Furthermore, functionalizing the liposome with lipid-anchored ligands binds to the specific surface receptors on different types of ganglion cells. Appropriate vesicle fusion proteins may be included in the liposomes to effect more efficient fusion with the cell membrane.

Photovoltaic FAN modulation of nerve cell trans-membrane potential, and inducing firing of action potential Illumination of photovoltaic FANs embedded in nerve cell membranes triggers the firing of the nerve cell action potential. A cell with an embedded semiconductor/metal FAN can be approximated electrically by the circuit diagram shown in FIG. 5 (lower portion). Membranes typically average ~5 nm in thickness and act as a capacitor (capacitance CM ~1 μF/cm$^2$). Membrane ion channels (mainly resting K$^+$ channels) exert a typical resistivity of R$_K$=10 kΩ·cm$^2$. The ionic gradient across the membrane, created by ATP driven ion-transporters, generates an electromotive potential (resting potential) inside the cell ~60 mV less than that outside.

An embedded semiconductor/metal FAN (with the metal inside the cell) acts as a photovoltaic cell, which is electrically equivalent to a current source with a resistor and a capacitor in parallel (FIG. 5, lower portion), with the parallel resistor representing the internal resistance within the FAN. The electric current varies with the rate of photon absorption. The connection between the FAN and the membrane is mediated by the motion of ions in the solution, which is represented by a series resistor between the FAN and the membrane.

Illumination of embedded photovoltaic FANs generate a photovoltage that reduces the potential across the ganglion cell membrane by ~10 mV. Such membrane depolarization causes enough voltage-sensitive Na$^+$ ion channels to open to generate an action potential that travels down the axon.

The density of FANs and the light flux to create the 10 mV membrane depolarization can be estimated as follows. A typical FAN consists of a 5 nm diameter gold tip grown on a 10 nm diameter CdSe nanorod and embedded in the membrane at a density of 10$^{10}$/cm$^2$. Since the FAN occupies only 1% of the membrane area, its capacitance is much smaller than that of the membrane. Such a FAN has ~10 nm$^2$ absorption cross-section for visible light.

For every photogenerated electron-hole separation across the plasma membrane (and assuming no electron-hole recombination, i.e., R$_{parallel}$>>R$_K$+R$_{Serial}$), generation of one action potential (by charging the membrane 10 mV) every second entails 10$^{-8}$ C/cm$^2$ charge displacement across the membrane per second.

This in turn implies 0.02 mW/cm$^2$ light power density impinging on the membrane of retinal ganglion cells. In typical human eyes only 20% of the incident light reaches the retina. Therefore to achieve 0.02 mW/cm$^2$ power density impinging on the retina, an eye with 4 mm pupil aperture needs to look at a light source of brightness 20,000 Cd/m$^2$. For reference objects in direct sunlight have typical brightness on the order of ~50,000 Cd/m$^2$.

Having generally described this invention, a further understanding can be obtained by reference to certain specific examples which are provided herein for purposes of illustration only and are not intended to be limiting unless otherwise specified.

The examples that follow focus on the use of CdSe/Au hetero-junctions for the sake of concreteness, but it will be readily appreciated by those skilled in the relevant art that FANs can be constructed from a variety of other semiconductor/metal and semiconductor/semiconductor hetero-junctions. For example, FANs based upon semiconductor/metal hetero-junctions between group II-VI, IV, III-V, IV-VI (referring to groups of the periodic table), metal-oxide, or organic semiconductors and a metal, and in particular those based upon Si/Au, GaAs/Au, InAs/Au, and PbS/Au hetero-junctions, can be used in the same way as those discussed here.

EXAMPLES

FIG. 8 shows high-resolution transmission electron microscopy images of CdSe/Au nanometer-sized semiconductor/metal hetero-junctions. Both CdSe and gold nanocrystals have individually been widely applied in biological labeling in cells, tissues, and animals. Integration of both CdSe and Au into one nanometer-sized composite leads to nanoscale Schottky diodes.

The CdSe/Au integrated nanometer-sized composites are synthesized through a two-step procedure. First, CdSe nanorods were formed by the reaction of Cd and Se precursors in a mixture of trioctylphosphine oxide and an alkylphosphonic acid. Due to the Wurtzite crystallographic structure of the CdSe, (001) and (00$\bar{1}$) facets of the CdSe have enhanced chemical reactivity compared to the {011} facets, therefore rod-shaped CdSe nanoparticles (elongated along (001) direction) can be formed.

Second, the CdSe rods suspension is treated with a mixture of gold chloride, didodecyldimethyl-ammonium bromide, and hexadecylamine to stabilize the nanocrystals and to reduce the gold chloride to elemental gold.

Because the two ends ((001) vs. (00$\bar{1}$) facets) of the CdSe rods differ crystallographically (and hence chemically), careful control of growth conditions allows growth of Au particles preferentially on one end of each rod.

In FIG. 8 the dark end of the rod corresponds to the Au tip, which has higher electron density than the CdSe end. The particle size (<2 nm to >100 nm), aspect ratio (1:1 to >1:30) or shape (rod, tetrapod) can be varied over a wide range by controlling growth conditions.

Photovoltaic FANs

Transient electrical birefringence measurements confirm the photovoltaic effect in the CdSe/Au nanometer-sized semiconductor/metal hetero-junctions. CdSe rods exhibit optical birefringence owing to their anisotropy. Transient electrical birefringence measurements entail measuring the rise (Δnr) and fall (Δnf) of the birefringence of the CdSe rods or CdSe/Au nanometer-sized heterojunctions (suspended in a liquid) in response to the imposition and removal of an external electric field. The rising edge of the birefringence of the rods reflects the rotation of nanometer-sized hetero-junctions to align its dipole preferentially with the external field. The falling edge, the slope of which gives the rotational diffusion constant of the rods, reflects the randomization of the rod orientation on removal of the external field. CdSe/Au samples of large aspect ratio were used to achieve sufficient transient electrical birefringence signal.

FIG. 9 shows the rising and FIG. 10 falling edge of the transient birefringence for three cases: CdSe rods before Au tip growth, and CdSe/Au hetero-junctions with and without excitation. Excitation was via continuous 532 nm laser at 1 W/cm$^2$. Heating by the excitation laser was considered and ruled out. Compared to CdSe rods, the fall and rise of CdSe/Au birefringence is ~20 times slower. Moreover, CdSe/Au samples in dark and under 532 nm illumination exhibited significantly different transient electrical birefringence. This different rotational response to an external electric field is consistent with photoexcitation redistributing charge in individual CdSe/Au nanometer-sized semiconductor/metal hetero-junctions, and therefore with a photovoltaic effect.

Probing FAN Photovoltaic Effect Using AFM Based Surface Potential Probing

The photovoltaic effect of the CdSe/Au FAN is also independently checked using atomic force microscopy (AFM) based surface potential probing (SPP) as schematically shown in FIG. 11. To prepare the sample for this measurement, a drop of CdSe/Au FAN solution in toluene was put onto a freshly cleaved surface of highly ordered pyrolytic graphite (HOPG) and placed in an constant electrical field of ~1×10$^4$ V/cm perpendicular to the HOPG surface. Since the CdSe/Au FANs have built-in electrical dipole, as the FAN solution slowly dries (over ~1 hour), the HOPG surface gets coated with a layer of FANs that statistically acquire a preferred orientation along the electrical field perpendicular to the surface.

The sample was then installed on a Digital Instrument Multimode AFM and an Platinum Iridium-coated conducting AFM tip was used to measure the surface potential ($V_{surface}$) of CdSe/Au FAN coated HOPG substrate under light excitation as briefly described below (refer to FIG. 11). The AFM tip was lifted a certain height (~60 nm) above the surface of the sample. A voltage $V(t)=V_{DC}+V_{AC}\cdot\sin(\omega t)$ was applied on the AFM tip (where $\omega$ is the resonant frequency of the tip) to create an oscillating electrical force between the tip and the surface. The surface potential ($V_{surface}$) was then measured by adjusting $V_{DC}$ to be equal to $V_{surface}$ via a feedback loop so that the force between the tip and surface at frequency $\omega$ was zeroed (hence the oscillation of the tip is minimized).

In our measurements, the FAN coated HOPG sample was excited by a 532 nm laser chopped at 10 Hz. The measured surface potential is shown in FIG. 12. The difference in the surface potential as the light excitation is turned on and off is around 15 mV. This difference can most likely be attributed to the photovoltaic effect of the CdSe/Au FANs on the HOPG surface, since no measurable surface potential change as a function of light excitation was observed on either bare HOPG or HOPG surface deposited with CdSe rods.

Rendering FANs Water-Compatible

Synthesis of the colloidal FANs preferably uses non-polar solvents such as toluene, whereas their use in vivo necessitates ultimately exposing them to water. Encapsulation of the FANs in phospholipid block-copolymer micelles composed of n-poly(ethylene glycol) phosphatidylethanolamine (PEG-PE) and phosphatidylcholine protected the FANs and thereby rendered them compatible with phosphate-buffered saline solution. U.S. Pat. No. 7,041,371 describes methodology for coating the surfaces of semiconductor nanoparticles with polyethylene glycol.

FIG. 13 shows the measured optical density of the as-synthesized FAN in toluene and then converted to soluble in phosphate-buffered saline for normalized concentration. Similar phospholipid micelle encapsulation of CdSe-based semiconductor quantum dots for in vitro and in vivo imaging applications rendered them stable in physiological solution and non-toxic to cells up to concentrations of $5\times10^9$ per dots/cell.

CdSe/Au Synthesis

Standard procedures were used to produce CdSe nanorods by reaction of Cd and Se precursors in trioctylphosphine oxide containing an alkylphosphonic acid. In the second step, Au precursors were added into the CdSe rod solution. The chemical difference of the two ends of the CdSe rods allows Au particles to be grown on one end preferentially by appropriate control of growth conditions.

CdSe Rod Synthesis Procedure

Selenium was dissolved in prepared by dissolving selenium in trioctylphosphine (Se/trioctylphosphine) 10% w/w). Cadmium oxide (200 mg), trioctylphosphine oxide (3 g), hexylphosphonic acid (0.16 g), and octadecylphosphonic acid (0.85 g) were heated to 330° C. in a flask under Ar on a Schlenk line. Rapid injection of ~0.62 g selenium/trioctylphosphine (10% w/w) at ~330° C. into the flask causes fast nucleation of the rods. After 50 min at ~300° C. to promote further growth of the rods the reaction was stopped, the produced CdSe rods dissolved in toluene, precipitated by methanol, and then redissolved in toluene for storage.

The rods are characterized through use of transmission electron microscopy. Varying the Se pre-cursor injection volume and concentration, the injection temperature, and the molar ratio of the trioctylphosphine oxide(TOPO):hexylphosphonic acid (HPA):octadecylphosphonic acid (ODPA) allows control over the length and width of the rods. Typically increased Se precursor injection concentration and increased injection temperature leads to formation of larger number of nuclei, therefore the average size of the nanorods decreases. Increased molar ratio of phosphonic acids (HPA and ODPA) to TOPO leads to formation of nanorods of larger aspect ratio.

Au/CdSe Nanocrystal Metal-semiconductor Junction Synthesis Procedure

The Au/CdSe nanocrystal semiconductor/metal junction was formed by growing Au tips on one end of the CdSe rods.

A stock solution of gold salts was prepared by dissolving $AuCl_3$ (1.66 mg), didodecyldimethyl ammonium bromide (8.33 mg), and hexyldecylamine (15 mg) in toluene (1 g).

To CdSe rods (20 g, synthesized as described above) diluted to 10 mg/mL with toluene under Ar was added ~1 mL of the stock solution of gold salts at a rate ~0.1 mL/min. Owing to the chemical difference of the two ends of the CdSe rods, Au particles can be grown on one end preferentially. The thereby-produced Au/CdSe nanocrystal semiconductor/metal junctions were precipitated with methanol, and then redissolved in anhydrous toluene or chloroform for storage.

The as-synthesized Au/CdSe rods were characterized through use of transmission electron microscopy. The majority (>75%) of Au/CdSe rods synthesized by the procedure outline above are asymmetric with only a single Au tip on the CdSe rod.

CdSe/Au Amphiphilic Surface Functionalization

As synthesized, the CdSe/Au rods are covered by trioctylphosphine oxide and alkylphosphonic acid (both of which are hydrophobic), as shown in FIG. 14. Surface functionalization covers the Au tips of the CdSe/Au rods with polyethylene glycol, making them hydrophilic; the CdSe end, still covered by trioctylphosphine oxide and alkyl phosphonic acid, remains hydrophobic (FIG. 15). Overall the CdSe/Au nanojunctions are amphiphilic and compatible with bilipid membranes.

CdSe/Au (~0.1 mg/mL) nanojunctions are suspended in N,N-dimethylformamide containing detergent (e.g., 1% Triton X-100) and exposed to polyethylene glycol-$(CH_2)_{10}$—SH (~1 mM) at room temperature for about an hour under stir to coordinate the thiol to the Au end. After the reaction, the Au/CdSe rods are separated from the solution through use of spin-filtration (filter pore size ~10 kDa). The separated FANs are redissolved in phosphate buffered saline containing Triton X-100.

Construction of CdSe/Au Containing Liposomes

Liposomes are prepared sonicating a commercially-available mixture of phosphatidyl choline/cholesterol/phosphatidyl glycerol/phosphatidyl inositol (in 8:10:1:1:2 molar ratio) in aqueous buffer (e.g., 20 mM sodium phosphate, 0.15 M NaCl, pH 7.4) at room temperature.

Amphiphilically functionalized CdSe/Au FANs are inserted into the liposomes through first de-stabilizing the preformed liposomes with a detergent (e.g., 1% Triton X-100), followed by addition of amphiphilic CdSe/Au FANs to the destabilized liposome suspension. The CdSe/Au FAN-containing liposomes are then reconstituted by gel-chromatography (through use of for example Sepharose 4B column in 20 mM sodium phosphate, 0.15 M NaCl, pH 7.4 buffer). The liposome size is characterized through use of dynamic light scattering, while the orientation and density of the FANs in the liposome are characterized through use of transmission electron microscopy.

Conjugation of Antibody to the Liposome

Selective delivery of liposomes to cells (e.g. retina ganglion cells) with specific surface receptors (e.g. retina ganglion cell specific Thy-1 receptor), is achieved by conjugating the liposome to the corresponding antibodies by the following procedure, in which the amine terminus of the heavy chain of the antibody is linked to the phosphatidyl glycerol component of the liposome via reductive amination-mediated conjugation technique as detailed in the following two steps.

Periodate Oxidation of the Phosphatidyl Glycerol Component of the Liposomes

To a suspension of liposomes containing CdSe/Au rods diluted to total lipid ~5 mg/mL in buffer, and 200 µl of 0.6 M aqueous sodium periodate is added for each milliliter of the liposome suspension. After stirring for 30 min at room temperature in the dark the oxidized liposomes are dialyzed against 20 mM sodium borate, 0.15 M NaCl pH 8.4 to remove the unreacted periodate. The liposome suspension is further purified through use of a column of Sephadex G-50.

Conjugation of Periodate-oxidized Liposomes to an Antibody

To 1 mL of a liposome suspension containing 5 mg/ml total lipid is added 0.5 mL of a solution of the antibody (e.g., anti-Thy1) dissolved in 20 mM sodium borate, 0.15 M NaCl, pH 8.4, at a concentration of ~10 mg/mL. After incubation for 2 h at room temperature is added 10 µl of a 2 M solution of sodium cyanoborohydride in water, and reduction allowed to proceed at 4° C. over-night. Gel filtration through a column of Sephadex G-50 removes unconjugated protein and excess cyanoborohydride from the liposome suspension.

OTHER EMBODIMENTS

The present invention clearly can be used to introduce photoresponsiveness to a wide variety of cells, and thereby not only to restore lost function but to impart new function to such cells. For example, through use of the present invention photoresponsiveness can be introduced to cells not normally responsive to light, and/or the range of photoresponsiveness can be extended beyond normally visible wavelengths (to, e.g., the near infrared).

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A method of modulating photoreactivity in a photoreactive cell, comprising:
   placing a functional abiotic nanosystem in the membrane of the cell in a transmembrane position,
   wherein said functional abiotic nanosystem is capable of being excited by a light to generate an electric potential to effect an action potential in the cell,
   wherein a first portion of the surface of said functional abiotic nanosystem is coated with a hydrophilic coating and a second portion of the surface of said functional abiotic nanosystem is coated with a hydrophobic coating, and
   whereby the photoreactivity of the cell is modulated via excitation of the nanosystem by light.

2. The method of claim 1, wherein the functional abiotic nanosystem is selected from the group consisting of nanometer-sized semiconductor/metal hetero-junctions and semiconductor/semiconductor hetero-junctions.

3. The method of claim 1, wherein the functional abiotic nanosystem is a nanometer-sized semiconductor/metal hetero-junction.

4. The method of claim 3, wherein the nanometer-sized semiconductor/metal hetero-junction is formed between a metal and a semiconductor wherein the semiconductor is selected from metal-oxide semiconductors, organic conductors, group II-VI semiconductors, group IV semiconductors, group III-V semiconductors, and group IV-VI semiconductor.

5. The method of claim 4, wherein the nanometer-sized semiconductor/metal hetero-junction is selected from the group consisting of CdSe/Au, Si/Au, GaAs/Au, InAs/Au, and PbS/Au hetero-junctions.

6. The method of claim 5, wherein the nanometer-sized semiconductor/metal hetero-junction is a CdSe/Au hetero-junction.

7. A method of modulating photoreactivity in a photoreactive cell, comprising:
   placing a functional abiotic nanosystem in the membrane of the cell in a transmembrane position by contacting the functional abiotic nanosystem with the cell,
   wherein a first portion of the surface of said functional abiotic nanosystem is coated with a hydrophilic coating and a second portion of the surface of said functional abiotic nanosystem is coated with a hydrophobic coating,
   wherein the coated functional abiotic nanosystem is embedded in the lipid membrane of a liposome prior to being contacted with the cell so that upon contacting, said functional abiotic nanosystem becomes incorporated into the cell's membrane, and wherein said functional abiotic nanosystem is capable of being excited by light to generate an electric potential to effect an action potential in the cell, whereby excitation of the functional abiotic nanosystem results in modulation of the cell's photoreactivity.

8. The method of claim 1, wherein the cell is a eukaryotic cell.

9. The method of claim 8, wherein the eukaryotic cell is from a mammal.

10. The method of claim 9, wherein the cell is selected from the group consisting of nerve cells, retinal ganglion cells, retinal bipolar cells, photoreceptor cells, and retinoblastoma cells.

11. The method of claim 10, wherein the cell is a retinal ganglion cell.

12. The method of claim 1, wherein the functional abiotic nanosystem responds to electromagnetic radiation.

13. The method of claim 12, wherein the electromagnetic radiation has a wavelength between about 200 nm and about 2000 nm.

14. The method of claim 13, wherein the electromagnetic radiation has a wavelength between about 350 nm and about 1000 nm.

15. The method of claim 14, wherein the electromagnetic radiation has a wavelength between about 400 nm and 800 nm.

16. The method of claim 1, wherein the membrane is selected from the group consisting of plasma membranes and organelle membranes.

17. The method of claim 16, wherein the membrane is a plasma membrane.

18. A method for endowing photosensitivity to an optic nerve cell, comprising:
   introducing a functional abiotic nanosystem to the cell in a transmembrane position, wherein said functional abiotic nanosystem comprises a nanometer-sized semiconductor/metal hetero-junction or a semiconductor/semiconductor hetero-junction, and a first portion of the surface of said functional abiotic nanosystem is coated with a hydrophilic coating and a second portion of the surface of said functional abiotic nanosystem is coated with a hydrophobic coating.

19. The method of claim 18, wherein said introducing step comprises encapsulating the functional abiotic nanosystem in a liposome and fusing the liposome with the cell.

* * * * *

UNITED STATES PATENT AND TRADEMARK OFFICE
CERTIFICATE OF CORRECTION

PATENT NO. : 8,399,751 B2
APPLICATION NO. : 12/138289
DATED : March 19, 2013
INVENTOR(S) : Siyuan Lu, Anupam Madhukar and Mark S. Humayun Page 1 of 1

It is certified that error appears in the above-identified patent and that said Letters Patent is hereby corrected as shown below:

In the Specification

Column 1, Lines 16-20 delete:
"The U.S. Government has certain rights in this invention pursuant to grant No. EEC-0310723, awarded by the National Science Foundation, Engineering Research Centers Program and AFOSR 49620-01-0474 awarded by the Department of Defense."
Insert:
--This invention was made with government support under F49620-01-1-0474 awarded by the Air Force Office of Scientific Research, and EEC0310723 awarded by the National Science Foundation. The government has certain rights in the invention.--

Signed and Sealed this
Twentieth Day of August, 2024

Katherine Kelly Vidal
*Director of the United States Patent and Trademark Office*